(12) United States Patent
Facchetti et al.

(10) Patent No.: US 9,067,886 B2
(45) Date of Patent: Jun. 30, 2015

(54) COMPOUNDS HAVING SEMICONDUCTING PROPERTIES AND RELATED COMPOSITIONS AND DEVICES

(71) Applicant: Polyera Corporation, Skokie, IL (US)

(72) Inventors: Antonio Facchetti, Chicago, IL (US); Hakan Usta, Evanston, IL (US); Jingqi Wang, Evanston, IL (US); Chun Huang, Skokie, IL (US); Christopher Newman, Evanston, IL (US)

(73) Assignee: Polyera Corporation, Skokie, IL (US)

( * ) Notice: Subject to any disclaimer, the term of this patent is extended or adjusted under 35 U.S.C. 154(b) by 104 days.

(21) Appl. No.: 13/683,949

(22) Filed: Nov. 21, 2012

(65) Prior Publication Data
US 2013/0146851 A1    Jun. 13, 2013

Related U.S. Application Data

(60) Provisional application No. 61/562,683, filed on Nov. 22, 2011.

(51) Int. Cl.
| | | |
|---|---|---|
| C07D 519/00 | (2006.01) | |
| C07D 209/58 | (2006.01) | |
| C07D 209/80 | (2006.01) | |
| H01L 51/00 | (2006.01) | |
| C07D 487/04 | (2006.01) | |
| C07D 495/14 | (2006.01) | |
| C07D 495/22 | (2006.01) | |
| H01L 51/05 | (2006.01) | |

(52) U.S. Cl.
CPC ............ C07D 209/80 (2013.01); *C07D 519/00* (2013.01); *C07D 209/58* (2013.01); H01L 51/0071 (2013.01); H01L 51/0072 (2013.01); *H01L 51/0558* (2013.01); C07D 487/04 (2013.01); C07D 495/14 (2013.01); C07D 495/22 (2013.01); *H01L 51/0045* (2013.01)

(58) Field of Classification Search
CPC ... C07D 519/00; C07D 209/58; C07D 209/80
USPC ......................................... 548/417, 418, 421
See application file for complete search history.

(56) References Cited

U.S. PATENT DOCUMENTS

| | | | |
|---|---|---|---|
| 5,936,259 A | 8/1999 | Katz et al. ........................ | 257/40 |
| 8,101,776 B2 | 1/2012 | Berens et al. .................. | 548/148 |
| 2011/0220884 A1 | 9/2011 | Saito et al. ........................ | 257/40 |
| 2011/0240978 A1 | 10/2011 | Lim et al. ......................... | 257/40 |
| 2011/0260114 A1 | 10/2011 | Wu et al. ......................... | 252/500 |

FOREIGN PATENT DOCUMENTS

| | | |
|---|---|---|
| EP | 2298739 | 3/2011 |
| EP | 2298771 | 1/2012 |
| JP | 11-195790 | 7/1999 |
| WO | 2007/068618 | 6/2007 |
| WO | 2009/113599 | 9/2009 |
| WO | 2011/102586 | 8/2011 |

*Primary Examiner* — Shawquia Jackson
(74) *Attorney, Agent, or Firm* — Karen K. Chan

(57) ABSTRACT

Disclosed are new compounds having semiconducting properties. Such compounds can be processed into thin film semiconductors that exhibit high carrier mobility and/or good current modulation characteristics.

20 Claims, 2 Drawing Sheets

A)

B)

US 9,067,886 B2

COMPOUNDS HAVING SEMICONDUCTING PROPERTIES AND RELATED COMPOSITIONS AND DEVICES

CROSS REFERENCE TO RELATED APPLICATIONS

This application claims priority to and the benefit of U.S. Provisional Patent Application Ser. No. 61/562,683, filed on Nov. 22, 2011, the disclosure of which is incorporated by reference herein in its entirety.

BACKGROUND

Organic optoelectronic devices such as organic thin film transistors (OTFTs), organic light emitting diodes (OLEDs), printable circuits, organic photovoltaic devices, capacitors and sensors are fabricated using small molecule or polymeric semiconductors as their active components. To achieve high speed performance and efficient operation, it is desirable that both the p-type and n-type semiconductor materials in these organic semiconductor-based devices exhibit high charge carrier mobility ($\mu$) and stability under ambient conditions, and can be processed in a cost-effective manner.

Accordingly, the art continues to desire new organic semiconductors, particularly those having good stability, processing properties, and/or charge transport characteristics in ambient conditions.

SUMMARY

In light of the foregoing, the present teachings relate to new semiconducting compounds that can exhibit properties such as good charge transport characteristics under ambient conditions, chemical stability, low-temperature processability, large solubility in common solvents, and processing versatility. As a result, field effect devices such as thin film transistors that incorporate the present compounds as the semiconductor layer can have high performance under ambient conditions, for example, demonstrating one or more of large electron mobilities, low threshold voltages, and high current on-off ratios.

In various embodiments, the present teachings provide pi-conjugated compounds comprising a pyrrole moiety at one or both ends. For example, compounds of the present teachings can be represented by either formula I or II:

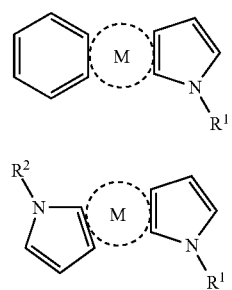

where M is a fused ring moiety comprising at least three and up to seven aromatic rings, where each aromatic ring is fused to two other aromatic rings; and $R^1$ and $R^2$ independently are selected from the group consisting of a $C_{1-40}$ alkyl group and a $C_{1-40}$ haloalkyl group.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF THE DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

DETAILED DESCRIPTION

Figure 1:
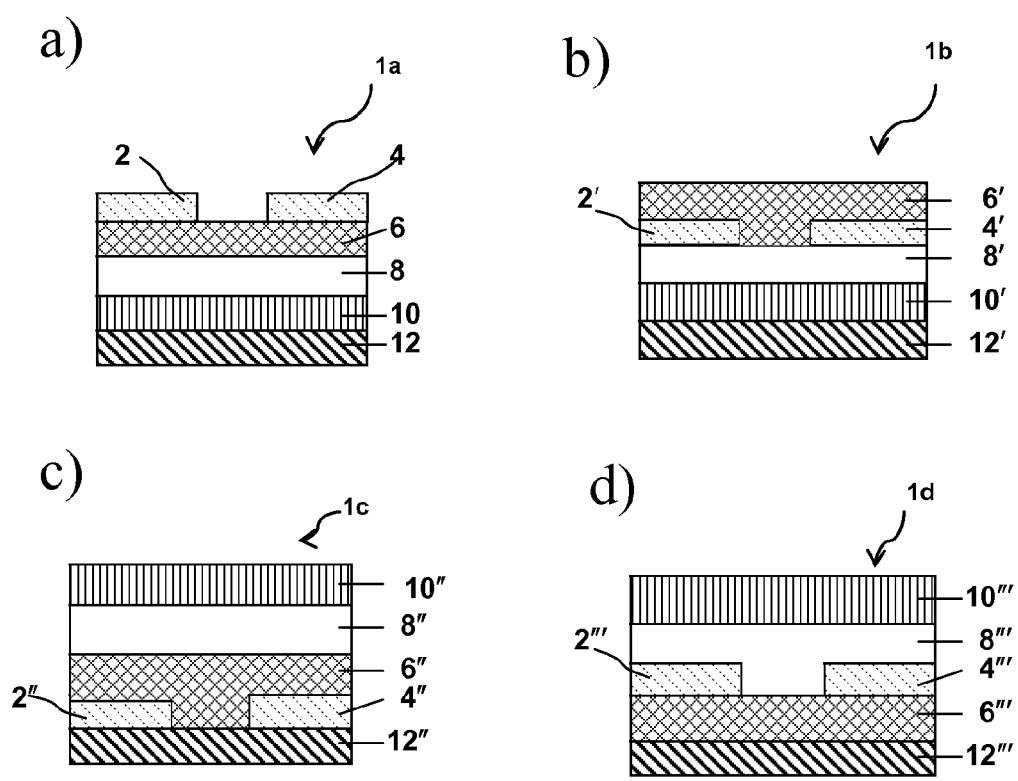
FIG. 1 illustrates four different configurations of thin film transistors: bottom-gate top contact (a), bottom-gate bottom-contact (b), top-gate bottom-contact (c), and top-gate top-contact (d); each of which can be used to incorporate compounds of the present teachings.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein.

As used herein, "alkylthio" refers to an —S-alkyl group (which, in some cases, can be expressed as —$S(O)_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl(bicyclic), 2-naphthyl(bicyclic), anthracenyl(tricyclic), phenanthrenyl(tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is defined as a divalent alky group that can be optionally substituted as described herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

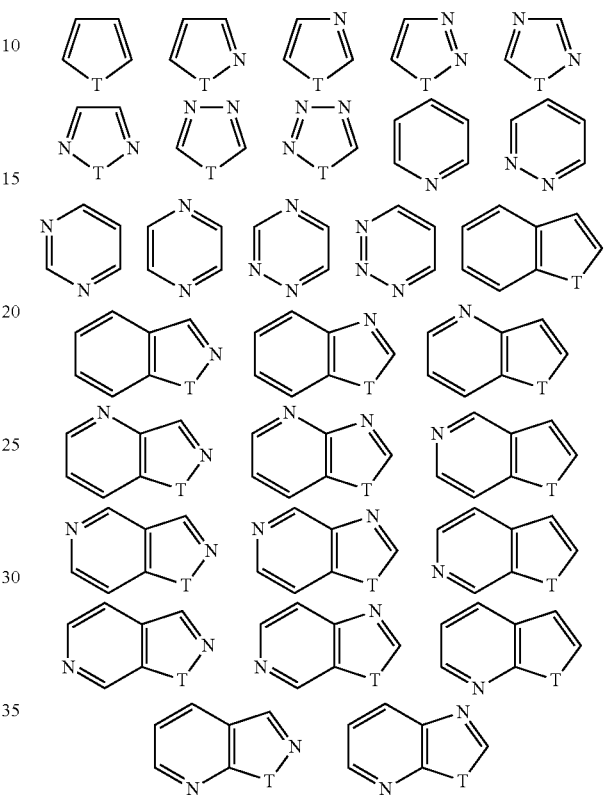

where T is O, S, NH, N-alkyl, N-aryl, N-(arylalkyl) (e.g., N-benzyl), $SiH_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^0)_2^+$, —$N(R^0)_3^+$, —$SO_3H$, —$SO_2R^0$, —$SO_3R^0$, —$SO_2NHR^0$, —$SO_2N(R^0)_2$, —COOH, —$COR^0$, —$COOR^0$, —$CONHR^0$, —$CON(R^0)_2$, $C_{1-40}$ haloalkyl groups, $C_{6-14}$ aryl groups, and 5-14 membered electron-poor heteroaryl groups; where $R^0$ is a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, —$OR^0$, —$NH_2$, —$NHR^0$, —$N(R^0)_2$, 5-14 membered electron-rich heteroaryl groups, $C_{1-40}$ alkyl groups, $C_{2-40}$ alkenyl groups, $C_{2-40}$ alkynyl groups, $C_{1-40}$ alkoxy groups, where $R^0$ is a $C_{1-40}$ alkyl group, a $C_{2-40}$ alkenyl group, a $C_{2-40}$ alkynyl group, a $C_{6-14}$ aryl group, or a $C_{3-14}$ cycloalkyl group.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ $cm^2/Vs$. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ $cm^2/Vs$. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

Throughout the specification, structures may or may not be presented with chemical names. Where any question arises as to nomenclature, the structure prevails.

The present teachings provide various semiconducting small molecule compounds as well as compositions and organic semiconductor materials prepared from such compounds and compositions. The organic semiconductor materials disclosed herein can exhibit useful electrical properties and can be solution-processable, e.g., spin-coatable and printable. The semiconductor materials disclosed herein can be used to fabricate various organic electronic articles, structures and devices, including field-effect transistors, unipolar circuitries, complementary circuitries, and photovoltaic devices.

More specifically, the present teachings relate to compounds having formula I or II:

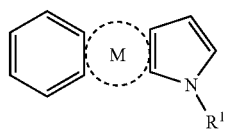

(I)

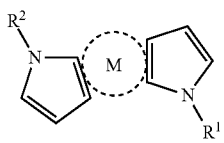

(II)

wherein M is a fused ring moiety comprising at least three and up to seven aromatic rings, where each aromatic ring is fused to two other aromatic rings; and $R^1$ and $R^2$ independently are selected from the group consisting of a $C_{1-40}$ alkyl group and a $C_{1-40}$ haloalkyl group. In various embodiments, the present teachings can exclude compounds having the formula:

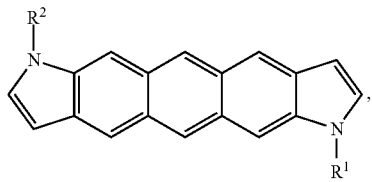

where $R^1$ and $R^2$ are as defined herein.

For example, M can be a fused ring moiety wherein the three, four, five, six or seven aromatic rings are fused and arranged in a linear or staggered configuration. In various embodiments, each of the aromatic rings can be a 5- or 6-membered ring. In certain embodiments, each of the aromatic rings can be carbocyclic (e.g., M can be an anthracenyl group or a phenanthrenyl group). In other embodiments, at least one of the aromatic rings can be heterocyclic and comprising at least one heteroatom selected from S, O, and Se. To illustrate, M can be a fused ring moiety comprising a thieno[3,2-b]thiophene moiety which optionally can be fused to additional aromatic rings at either or both ends that in turn are fused to the terminal pyrrole or phenyl ring. For example, M can be a dibenzothieno[3,2-b]thiophene moiety. In various embodiments, the aromatic ring immediately adjacent to the pyrrole moiety can be a phenyl group (hence, the compound can be terminated with an indole moiety at either or both ends).

To illustrate, certain compounds of the present teachings according to formula I can have a formula selected from:

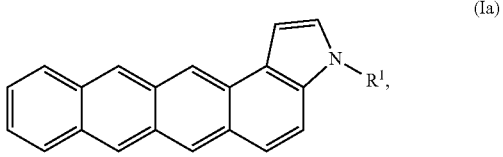

(Ia)

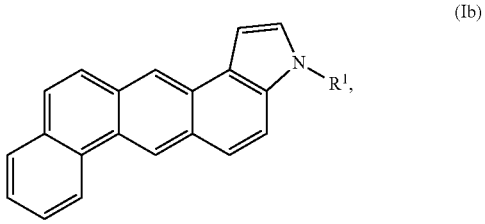

(Ib)

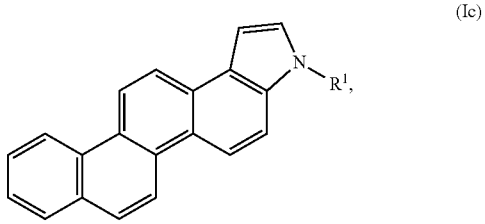

(Ic)

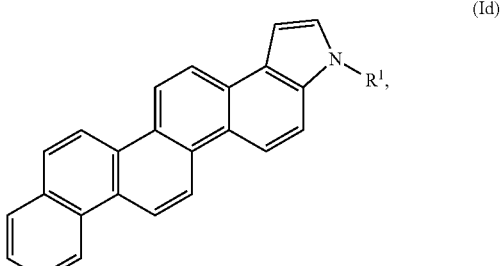

(Id)

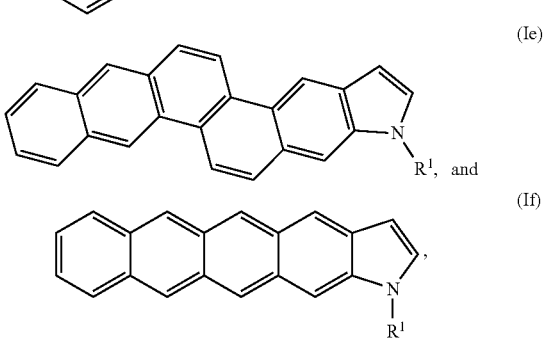

(Ie)

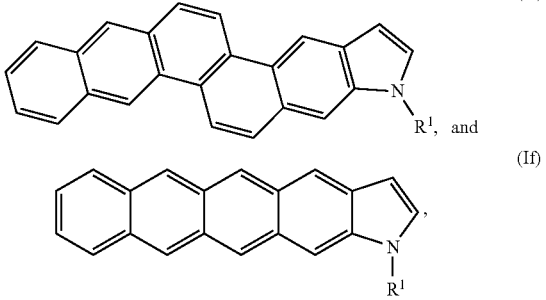

(If)

wherein $R^1$ is as defined herein.

In other embodiments, certain compounds of the present teachings according to formula I can have a formula selected from:

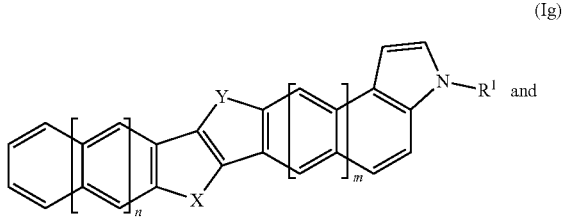

(Ig)

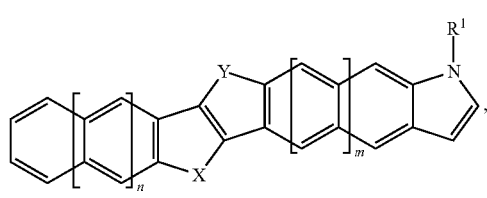

(Ih)

wherein:
X and Y independently are selected from S, O, and Se;
m and n independently are 0 or 1; and
$R^1$ is as defined herein.

For example, compounds according to formula (Ig) and (Ih) can include

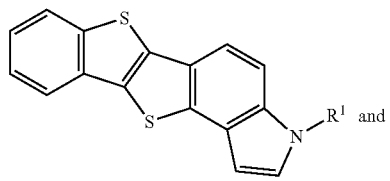

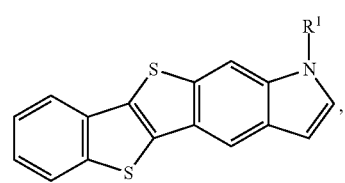

wherein X and Y are S; m and n are 0; and $R^1$ is as defined herein.

In various embodiments of compounds of formula (I), $R^1$ can be selected from a branched $C_{3-20}$ alkyl or haloalkyl group. For example, $R^1$ can be selected from:

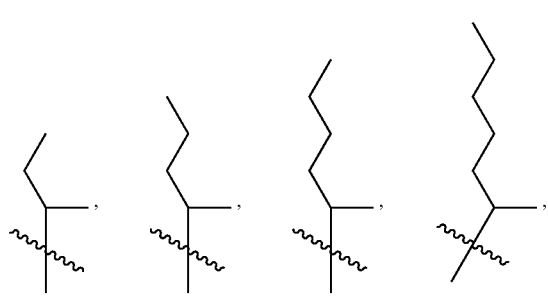

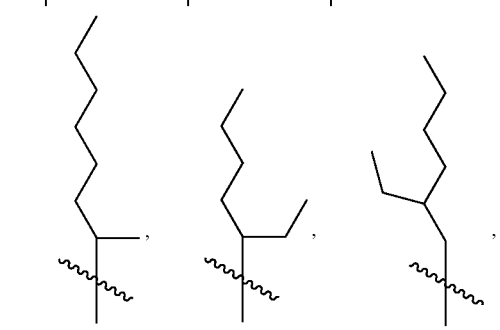

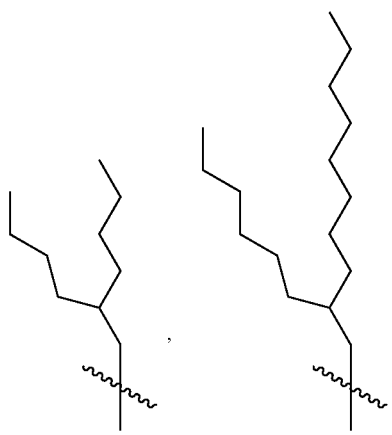

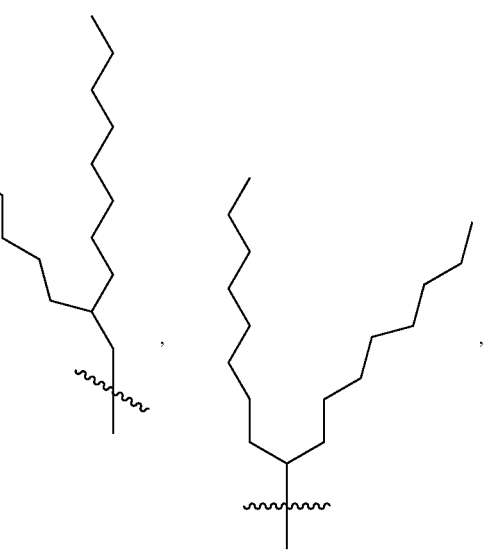

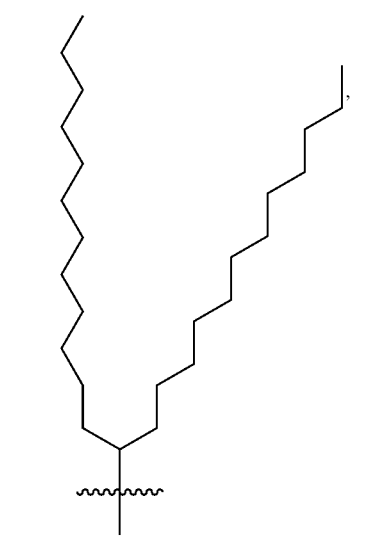

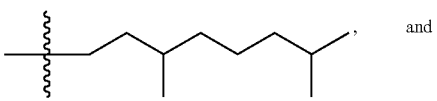

and

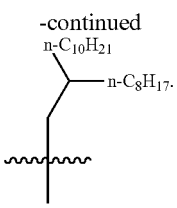

In particular embodiments, $R^1$ can be selected from a branched $C_{6-20}$ alkyl or $C_{6-20}$ haloalkyl group represented by:

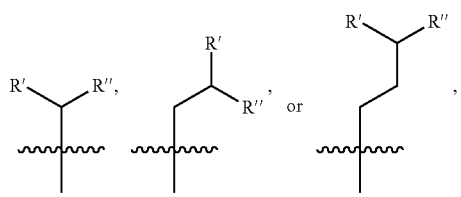

wherein R' can be selected from a linear $C_{3-12}$ alkyl group and a linear $C_{3-12}$ haloalkyl group; and R" can be selected from $CH_3$, $CF_3$, $C_2H_5$, $CH_2CF_3$, $CF_2CH_3$, and $C_2F_5$.

In other embodiments, certain compounds according to formula II can have a formula selected from:

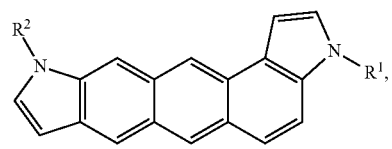
(IIa)

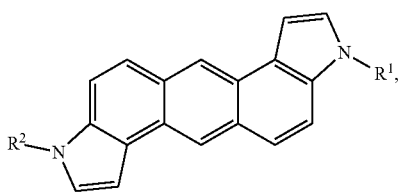
(IIb)

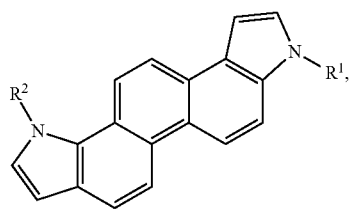
(IIc)

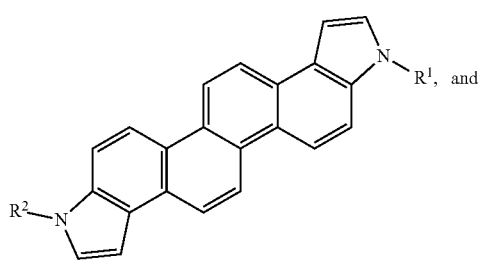
(IId), and

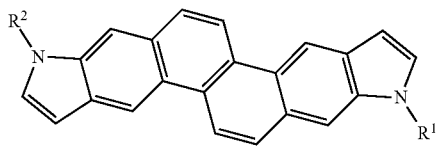
(IIe)

wherein $R^1$ and $R^2$ are as defined herein.

In other embodiments, certain compounds of the present teachings according to formula II can have a formula selected from:

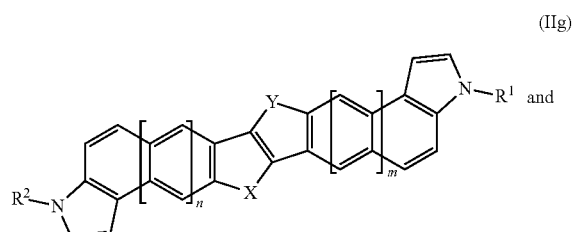
(IIg) and

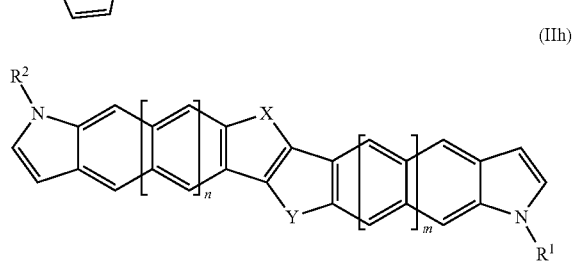
(IIh)

wherein:
X and Y independently are selected from S, O, and Se;
m and n independently are 0 or 1; and
$R^1$ and $R^2$ are as defined herein.

For example, compounds according to formula (IIg) and (IIh) can include

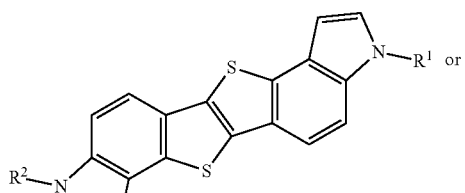
or

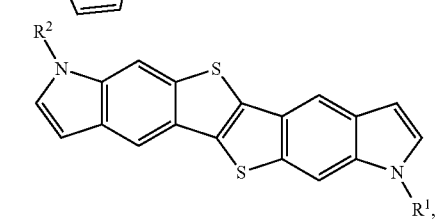

wherein X and Y are S; m and n are 0; and $R^1$ and $R^2$ are as defined in herein.

In various embodiments of compounds of formula (II), $R^1$ and $R^2$ independently can be selected from a branched $C_{3-20}$ alkyl or haloalkyl group. For example, $R^1$ and $R^2$ independently can be selected from:

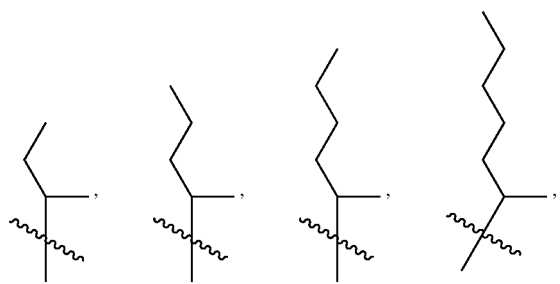

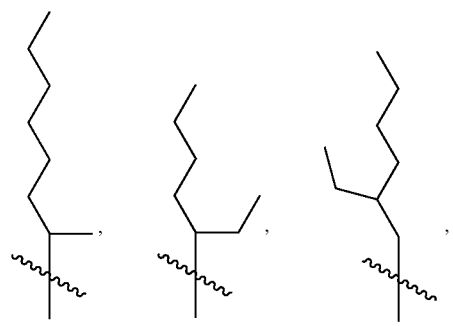

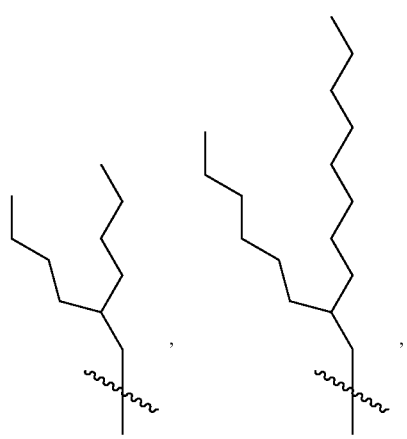

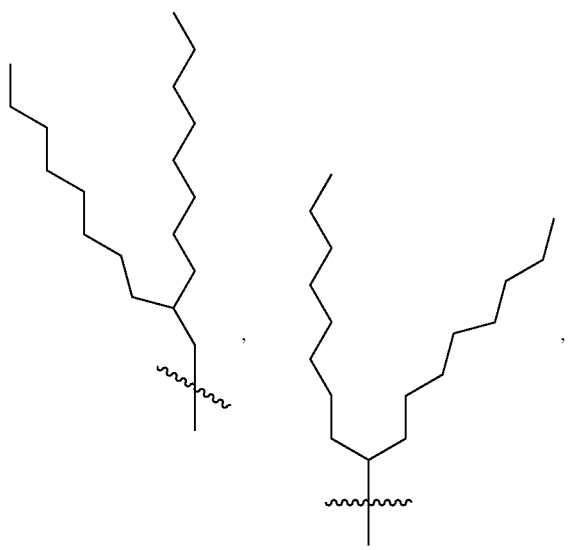

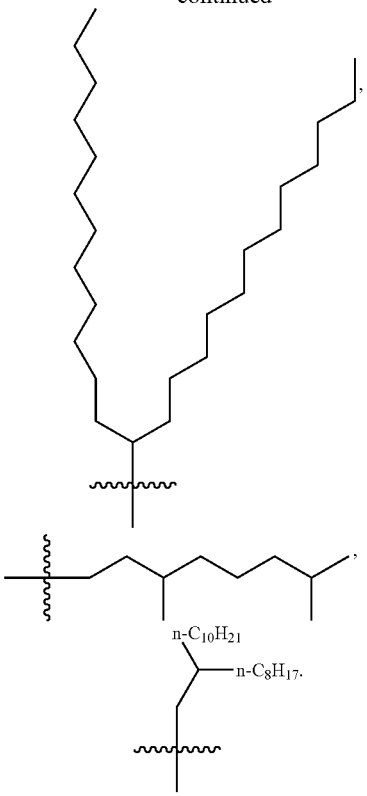

In particular embodiments, $R^1$ and $R^2$ independently can be selected from a branched $C_{6-20}$ alkyl or $C_{6-20}$ haloalkyl group represented by:

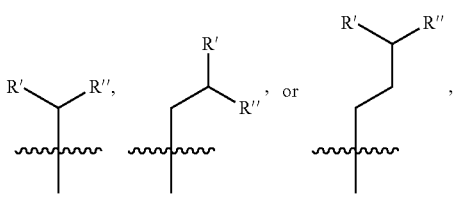

wherein R' can be selected from a linear $C_{3-12}$ alkyl group and a linear $C_{3-12}$ haloalkyl group; and R" can be selected from $CH_3$, $CF_3$, $C_2H_5$, $CH_2CF_3$, $CF_2CH_3$, and $C_2F_5$.

Compounds of the present teachings can be prepared according to procedures described in the Examples. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Various compounds according to the present teachings can have good charge transport properties and can be stable under ambient conditions ("ambient stable"), soluble in common solvents, and in turn solution-processable into various articles, structures, or devices.

Accordingly, the present teachings provide electronic devices, optical devices, and optoelectronic devices that include one or more compounds described herein as semiconductors. Examples of such electronic devices, optical devices, and optoelectronic devices include thin film semiconductors, thin film transistors (e.g., field effect transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators. In some embodiments, the present teachings provide for a thin film semiconductor including one or more compounds described herein and a field effect transistor device including the thin film semiconductor. In particular, the field effect transistor device has a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material includes an organic dielectric material, an inorganic dielectric material, or a hybrid organic/inorganic dielectric material. A plurality of such transistors can be connected electrically in an array, which in turn can be provided as a component of a display device (e.g., an electroluminescent display device). In other embodiments, the present teachings provide for photovoltaic devices and organic light emitting devices incorporating a thin film semiconductor that includes one or more compounds described herein.

As described above, compounds of the present teachings generally have good solubility in a variety of common solvents. Thus, various embodiments of the present compounds can be processed via inexpensive solution-phase techniques into electronic devices, optical devices, or optoelectronic devices. As used herein, a compound can be considered soluble in a solvent when at least 1 mg of the compound can be dissolved in 1 mL of the solvent. Examples of common non-chlorinated organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl)ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; and cyclic solvents such as cyclopentanone, cyclohexanone, and 2-methypyrrolidone.

Accordingly, the present teachings further provide compositions that include one or more compounds disclosed herein dissolved or dispersed in a fluid medium, for example, an organic solvent. In some embodiments, the composition can further include one or more additives independently selected from detergents, dispersants, binding agents, compatibilizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin coating, drop-casting, zone casting, dip coating, and blade coating.

The present compounds can exhibit versatility in their processing. Formulations including the present compounds can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes one or more compounds disclosed herein dissolved or dispersed in a fluid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more compounds disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying. In various embodiments, the depositing step can be carried out at low temperatures, for example, at a temperature less than about 100° C., or at about room temperature. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., *PNAS*, 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT: PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

FIG. 1 illustrates the four common types of OFET structures: (top left) bottom-gate top-contact structure, (top right) bottom-gate bottom-contact structure, (bottom left) top-gate bottom-contact structure, and (bottom right) top-gate top-contact structure. As shown, in each of the configurations, the semiconductor component is in contact with the source and drain electrodes, and the gate dielectric component is in contact with the semiconductor component on one side and the gate electrode on an opposite side.

In certain embodiments, OTFT devices can be fabricated with one or more compounds disclosed herein on doped silicon substrates, using $SiO_2$ as the dielectric, in top-contact geometries. In particular embodiments, the active semiconductor layer which incorporates one or more compounds disclosed herein can be deposited at room temperature or at an elevated temperature. In other embodiments, the active semiconductor layer which incorporates one or more compounds disclosed herein can be applied by spin-coating or printing as described herein. For top-contact devices, metallic contacts can be patterned on top of the films using shadow masks.

In certain embodiments, OTFT devices can be fabricated with one or more compounds disclosed herein on plastic foils, using polymers as the dielectric, in top-gate bottom-contact geometries. In particular embodiments, the active semiconducting layer which incorporates one or more compounds disclosed herein can be deposited at room temperature or at an elevated temperature. In other embodiments, the active semiconducting layer which incorporates one or more compounds disclosed herein can be applied by spin-coating or printing as described herein. Gate and source/drain contacts can be made of Au, other metals, or conducting polymers and deposited by vapor-deposition and/or printing.

In various embodiments, a semiconducting component incorporating one or more compounds disclosed herein can exhibit p-type semiconducting activity, for example, a hole mobility of $10^{-4}$ cm$^2$/V-sec or greater and/or a current on/off ratio ($I_{on}/I_{off}$) of $10^3$ or greater.

Other articles of manufacture in which one or more compounds disclosed herein can be useful include photovoltaics or solar cells. The present compounds can exhibit broad optical absorption and/or a tuned redox properties and bulk carrier mobilities. Accordingly, the present compounds can be used, for example, as a p-type semiconductor in a photovoltaic design, which includes an adjacent n-type semiconductor to form a p-n junction. In other embodiments, the present compounds can be used in an organic light emitting transistor, wherein the present compound can function as a p-type semiconductor and is present in an active layer together with an n-type semiconductor and a light emitting compound.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures Anhydrous tetrahydrofuran (THF) was distilled from sodium/benzophenone. Reactions were carried out in oven-dried glassware under nitrogen using anhydrous solvents unless otherwise noted. NMR spectra were recorded on a Varian Unity Plus 500 spectrometer ($^1$H, 500 MHz; $^{13}$C, 125 MHz). Electrospray mass spectrometry was performed on a Thermo Finnegan model LCQ Advantage mass spectrometer.

Example 1

Synthetic Route to Phenanthroindole (6)

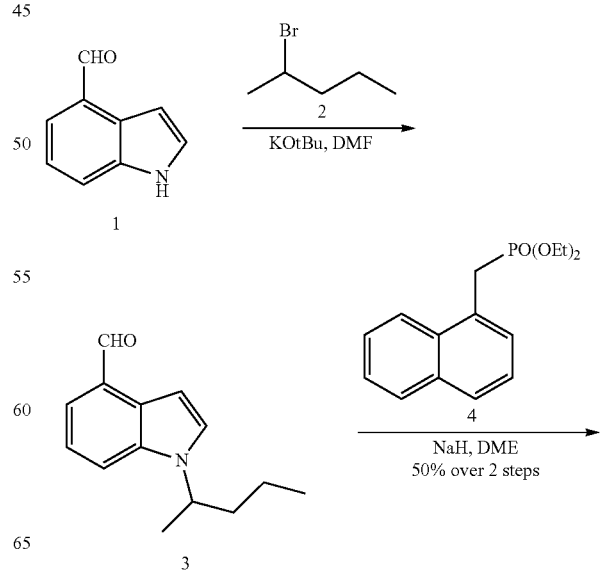

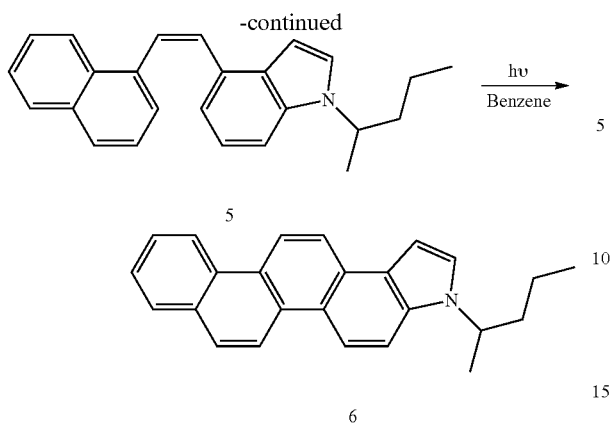

Synthesis of 1-(pentan-2-yl)-1H-indole-4-carbaldehyde (3)

To a solution of 1H-indole-4-carbaldehyde (1) (1.0 g, 6.88 mmol) in dimethylformamide (DMF, 35 mL) was added potassium t-butoxide (KOtBu, 1.16 g, 10.32 mmol) at 0° C. After the resulting solution was stirred for 30 min at 0° C., 2-bromopentane (2) (1.05 ml, 8.27 mmol) was added dropwise, and the reaction solution was warmed up to room temperature gradually and stirred for 12 h at room temperature. Water (5 ml) was added to quench the reaction. The reaction mixture was diluted with ethyl acetate (50 mL) and washed with H$_2$O (40 mL). The organic layer was dried over Na$_2$SO$_4$, filtered, and concentrated in vacuo. Purification by flash chromatography (6:1 hexane/ethyl acetate) recovered 1H-indole-4-carbaldehyde (1) (500 mg) and gave 1-(pentan-2-yl)-1H-indole-4-carbaldehyde (3) mixed with residual 2-bromopentane (2), which was used in the following step directly.

Synthesis of (Z)-4-(2-(naphthalen-1-yl)vinyl)-1-(pentan-2-yl)-1H-indole (5)

To a suspension of 95% sodium hydride (NaH, 347 mg, 13.76 mmol) in dimethyl ether (DME, 17 mL) was added diethyl(naphthalen-1-ylmethyl)phosphonate (4) (960 mg, 3.44 mmol) dropwise at 0° C. The resulting solution was stirred at room temperature for 1 h, then semi-pure 1-(pentan-2-yl)-1H-indole-4-carbaldehyde (3) (~3.44 mmol) in DME (2 mL) was added dropwise and the reaction mixture was stirred for 8 h at room temperature. After the reaction completed as indicated by thin layer chromatography, the reaction mixture was poured into ice-cold water (30 mL), extracted with ethyl acetate (3×30 mL), dried over Na$_2$SO$_4$, filtered, and concentrated in vacuo. Purification by flash chromatography (6:1 hexane/ethyl acetate) gave (Z)-4-(2-(naphthalen-1-yl)vinyl)-1-(pentan-2-yl)-1H-indole (5) (580 mg, 1.70 mmol) in 50% yield. $^1$H NMR (CDCl$_3$): 8.30 (d, 1H, J=8.0 Hz), 8.09 (d, 1H, J=16.0 Hz), 7.91 (dd, 1H, J=7.5, 1.5 Hz), 7.86 (d, 1H, J=7.0 Hz), 7.84 (d, 1H, J=8.0 Hz), 7.59 (d, 1H, J=16.0 Hz), 7.58-7.52 (m, 3H), 7.48 (d, 1H, J=7.0 Hz), 7.39 (d, 1H, J=8.0 Hz), 7.32 (d, 1H, J=3.5 Hz), 7.29 (d, 1H, J=7.5 Hz), 6.91 (d, 1H, J=3.0 Hz), 4.61-4.53 (m, 1H), 2.00-1.92 (m, 1H), 1.88-1.80 (m, 1H), 1.56 (d, 3H, J=7.0 Hz), 1.36-1.20 (m, 4H), 0.93 (t, 3H, J=7.5 Hz).

Synthesis of Phenanthroindole (6)

A solution of (Z)-4-(2-(naphthalen-1-yl)vinyl)-1-(pentan-2-yl)-1H-indole (5) (580 mg, 1.70 mmol) and I$_2$ (19 mg, 0.075 mmol) in benzene (150 mL) was irradiated using a Rayonet Reactor from Southern New England Ultraviolet Company (RPR-100 charged with 16×300 nm UV lamps) for 6 h. During the course of the reaction, the reaction flask was charged with a condenser and the reaction was open to air. After the completion, the reaction mixture was washed with saturated aqueous Na$_2$S$_2$O$_4$ (2×50 mL), dried over Na$_2$SO$_4$, filtered, and concentrated in vacuo. $^1$H NMR (CDCl$_3$): 8.76-8.74 (m, 2H), 8.69 (d, 1H, J=9.5 Hz), 8.50 (d, 1H, J=9.0 Hz), 8.41 (d, 1H, J=9.0 Hz), 7.93-7.90 (m, 2H), 7.68 (d, 1H, J=9.0 Hz), 7.64-7.60 (m, 1H), 7.54-7.51 (m, 1H), 7.27 (d, 1H, J=3.5 Hz), 7.11 (d, 1H, J=3.5 Hz), 4.64-4.57 (m, 1H), 1.96-1.87 (m, 1H), 1.84-1.77 (m, 1H), 1.54 (d, 3H, J=6.5 Hz), 1.14-1.27 (m, 4H), 0.84 (t, 3H, J=7.5 Hz).

Example 2

Synthetic Route to Bis-InBTBT (16)

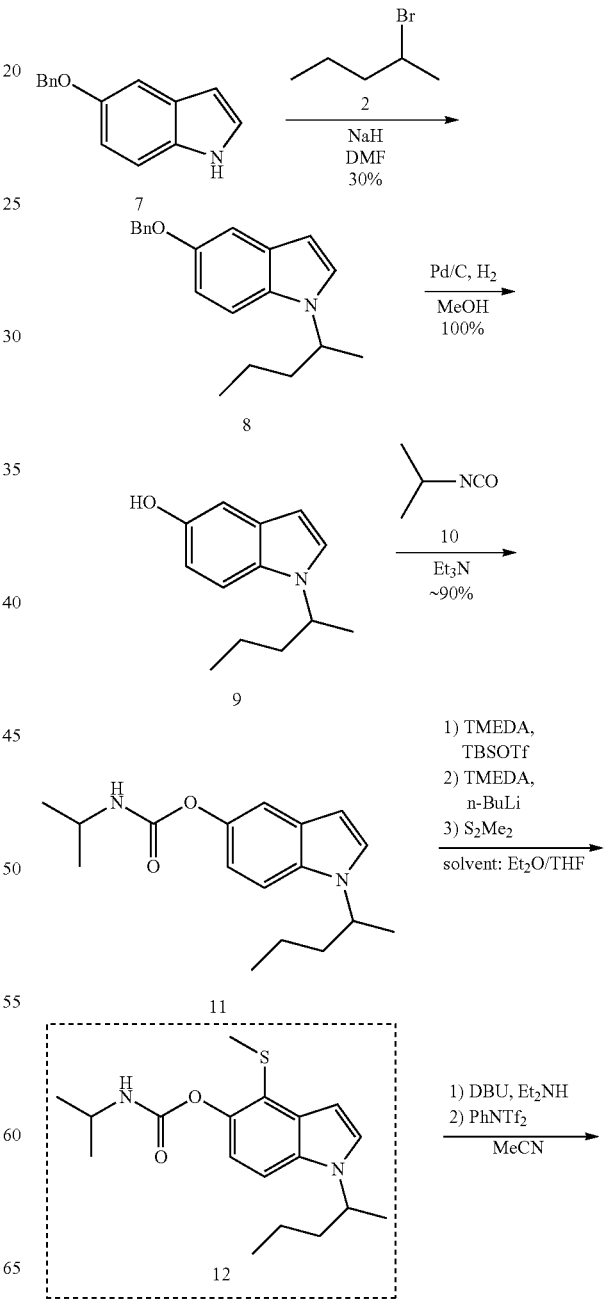

-continued

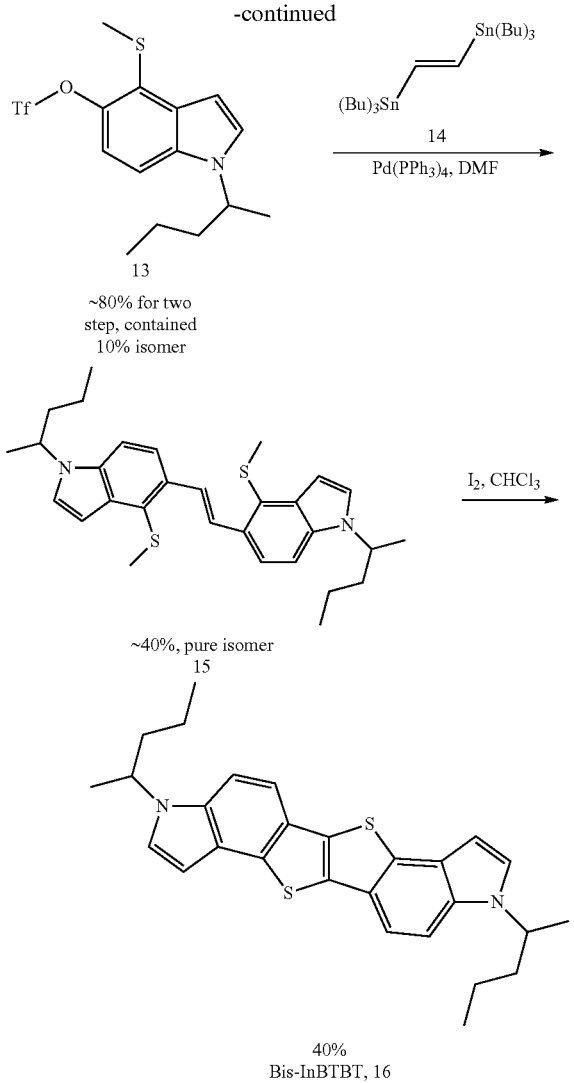

~80% for two step, contained 10% isomer

~40%, pure isomer 15

40% Bis-InBTBT, 16

Synthesis of 5-(benzyloxy)-1-(pentan-2-yl)-1H-indole (8)

95% NaH (2.15 g, 89.0 mmol) and 5-benzyloxyindole (7) (10.0 g, 44.8 mmol) were added to a schlenk vessel, and the system was evacuated and refilled with nitrogen three times before being cooled to −78° C. DMF (100 mL) was added and the vessel was then cooled with an ice/water bath and kept stirring for another 30 min. 2-Bromopentane (2) (10.2 g, 67.2 mmol) was added dropwise and the resulting mixture was warmed to room temperature slowly and kept stirring overnight. The solvent was removed in vacuo. Toluene (200 mL) was added and the mixture was washed with water (150 mL) and dried with $Na_2SO_4$. After solvent was removed in vacuo, the resulting oil was purified using silica column chromatography (1:1 chloroform/hexanes) to give 5-(benzyloxy)-1-(pentan-2-yl)-1H-indole (8) (3.90 g, 30%) as an oil. $^1$H NMR (500 MHz, $CDCl_3$): δ 7.51 (d, J=7.5, 2H), 7.41 (t, J=8.0 Hz, 2H), 7.35-7.20 (m, 2H), 7.18 (dd, J=8.0, 2.0, 2H), 6.97 (dd, J=9.0, 2.5, 1H), 6.41 (d, J=3.0, 1H), 5.13 (s, 2H), 4.46 (m, 1H), 1.87 (m, 2H), 1.55 (d, J=7.5, 3H), 1.26 (m, 2H), 0.90 (t, J=7.5, 3H). See also Luo, J.; Hart, H.; *J. Org. Chem.*, 52(22): 4833 (1987).

Synthesis of 1-(pentan-2-yl)-1H-indol-5-ol (9)

5-(Benzyloxy)-1-(pentan-2-yl)-1H-indole (8) (3.80 g, 12.9 mmol) was dissolved in methanol (MeOH, 30.0 mL) and 10% palladium on activated charcoal (Pd/C, 1.37 g, 0.129 mmol, 10 mol % Pd) was added. The mixture was placed under an atmosphere of hydrogen (double balloon), stirred overnight at room temperature, and then filtered over Celite® (MeOH eluent, 500 mL). Evaporation of the solvent under reduced pressure afforded 1-(pentan-2-yl)-1H-indol-5-ol (9) (2.60 g, 100%) as an oil. $^1$H NMR (500 MHz, $CDCl_3$): δ 7.25 (d, J=9.0, 1H), 7.18 (d, J=3.0 Hz, 1H), 7.05 (d, J=2.0 Hz, 1H), 6.80 (dd, J=9.0, 2.0, 1H), 6.41 (d, J=3.0 Hz, 1H), 4.56 (bs, 1H), 4.43 (m, 1H), 1.87 (m, 2H), 1.52 (d, J=6.5, 3H), 1.26 (m, 2H), 0.90 (t, J=7.5, 3H).

Synthesis of 1-(pentan-2-yl)-1H-indol-5-yl isopropylcarbamate (11)

To a stirred solution of 1-(pentan-2-yl)-1H-indol-5-ol (9) (2.60 g, 12.8 mmol) in dichloromethane ($CH_2Cl_2$, 40 mL) was added isopropyl isocyanate (10) (i-PrNCO, 1.63 g, 19.3 mmol), followed by triethylamine ($NEt_3$, 0.90 mL). The solution was stirred at room temperature overnight, and then concentrated to dryness in vacuo. The resulting oil was purified by silica gel column chromatography (1:3 ethyl acetate/hexanes) to provide 1-(pentan-2-yl)-1H-indol-5-yl isopropylcarbamate (11) (3.6 g, 98%) as a white solid. $^1$H NMR (500 MHz, $CDCl_3$): δ 7.35 (d, J=2.0, 1H), 7.32 (d, J=9.0 Hz, 1H), 7.22 (d, J=3.0 Hz, 1H), 6.98 (dd, J=8.5, 2.0, 1H), 6.50 (d, J=3.0 Hz, 1H), 4.86 (d, J=6.5 Hz, 1H), 4.49 (m, 1H), 3.82 (m, 1H), 1.87 (m, 2H), 1.51 (d, J=6.5, 3H), 1.26 (m, 8H), 0.90 (t, J=7.5, 3H).

Synthesis of 4-(methylthio)-1-(pentan-2-yl)-1H-indol-5-yl trifluoromethanesulfonate (13)

To a solution of 1-(pentan-2-yl)-1H-indol-5-yl isopropylcarbamate (11) (1.73 g, 6.0 mmol) and tetramethylethylenediamine (TMEDA, 1.30 mL) in a 3:1 mixture (80 mL) of diethyl ether ($Et_2O$) and tetrahydrofuran (THF) at 0° C. was added a solution of tert-butyldimethylsilyl trifluoromethanesulfonate (TBSOTf, 1.95 g, 7.3 mmol) in n-pentane (10.0 mL). After stirring for 5 min, the white suspension was allowed to warm to room temperature over 30 min. TMEDA (2.0 mL) was added, and the mixture was cooled to −78° C. A solution of n-butyllithium (n-BuLi) in hexanes (2.50 M, 7.2 mL, 18 mmol) was added dropwise. The mixture was stirred at −78° C. for 3 h, then neat 1,2-dimethyldisulfane ($S_2Me_2$, 4.3 g, 46 mmol) was added dropwise. The resulting mixture was allowed to warm to 23° C. slowly and kept stirring overnight. The mixture was washed successively with a saturated aqueous sodium hydrogen sulfite solution ($NaHSO_4$, 1×50 mL) and brine (1×50 mL), then dried over $Na_2SO_4$. Evaporation under reduced pressure afforded an oil (12) which was dissolved in acetonitrile (MeCN, 45 mL) and the mixture was added 1,8-diazabicyclo[5.4.0]undec-7-ene (DBU, 2.23 mL) and diethylamine ($Et_2NH$, 0.80 mL). The resulting mixture was placed in a heating bath maintained at 40° C. for 50 min, then allowed to cool to room temperature. Next, a solution of N-phenyl-bis(trifluoromethanesulfonimide) ($PhNTf_2$, 2.60 g, 7.28 mmol) in MeCN (10 mL) was added. After stirring for 80 min, the solvent was removed in vacuo. The resulting oil was purified by silica gel column chromatography (1:1 hexanes/chloroform) to provide 4-(methylthio)-1-(pentan-2-yl)-1H-indol-5-yl trifluoromethanesulfonate (13) (2.0 g, 87% with ~10% isomer). $^1$H NMR (500

MHz, CDCl$_3$): δ 7.43 (d, J=3.0, 1H), 7.41 (d, J=9.0 Hz, 1H), 7.11 (d, J=9.0 Hz, 1H), 6.82 (d, J=3.0, 1H), 4.52 (m, 1H), 2.51 (s, 3H), 1.87 (m, 2H), 1.53 (d, J=7.0, 3H), 1.26 (m, 8H), 0.91 (t, J=7.5, 3H).

Synthesis of (E)-1,2-bis(4-(methylthio)-1-(pentan-2-yl)-1H-indol-5-yl)ethane (15)

To a deaerated solution of 4-(methylthio)-1-(pentan-2-yl)-1H-indol-5-yl trifluoromethanesulfonate (13) (1.2 g, 3.0 mmol) and trans-1,2-bis(tributylstannyl)ethene (14) (0.91 g, 1.5 mmol) in DMF (10 mL) was added tetrakis(triphenylphosphine) palladium (Pd(PPh$_3$)$_4$, 86 mg, 0.075 mmol). The mixture was heated at 120° C. for 18 h in dark and then concentrated to dryness in vacuo. The residual was purified by silica gel column chromatography (2:3 hexanes/chloroform) to give (E)-1,2-bis(4-(methylthio)-1-(pentan-2-yl)-1H-indol-5-yl)ethane (15) (0.44 g, 30%) as a yellow oil. $^1$H NMR (500 MHz, CD$_2$Cl$_2$): δ 7.31 (d, J=9.0, 2H), 7.26 (d, J=3.5 Hz, 2H), 7.17 (d, J=8.5 Hz, 2H), 6.60 (s, 2H), 6.59 (d, J=3.5 Hz, 2H), 4.46 (m, 2H), 2.32 (s, 6H), 1.87 (m, 4H), 1.51 (d, J=6.5, 3H), 1.26 (m, 4H), 0.90 (t, J=7.0, 3H). See also Sygula, A.; Sygula, R.; Rabideau, P. W.; *Org. Lett.*, 8:5909 (2006).

Synthesis of bis-InBTBT (16)

Powder iodine (4.1 g, 16 mmol) was added to a schlenk vessel containing a solution of compound (15) (250 mg, 0.51 mmol) in chloroform (20 mL), and the mixture was heated to reflux for 20 h. Chloroform (80 mL) was added and saturated aqueous NaHSO$_4$ (20 mL×3) and water 920 mL were used to wash the mixture subsequently. The solvent was removed in vacuo. The resulting oil was purified by silica gel column chromatography (1:1 hexanes/chloroform) to provide bis-InBTBT (16) (92 mg, 40% yield) as a yellow solid.

Example 3

Synthetic Route to Mono-InBTBT (20)

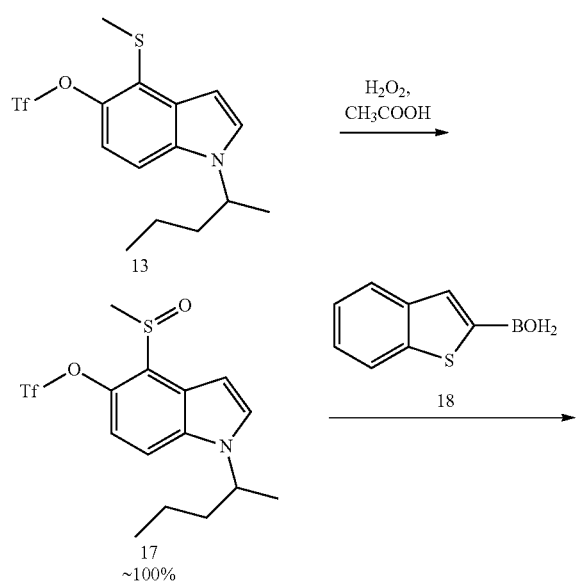

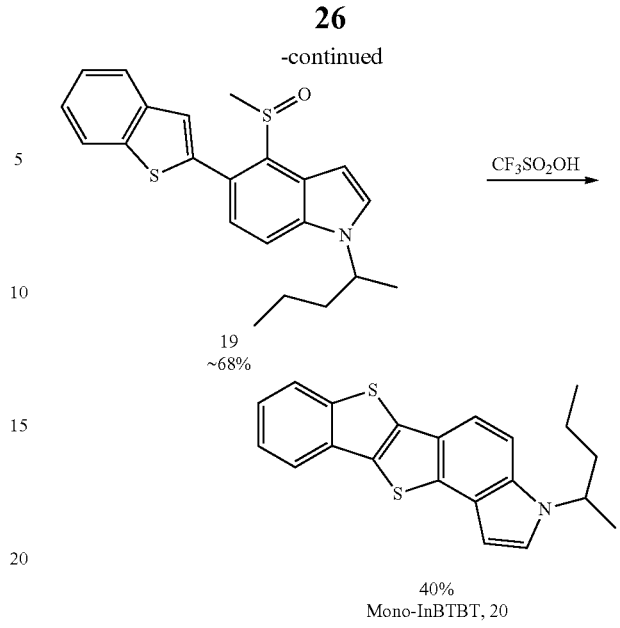

Synthesis of 4-(methylsulfinyl)-1-(pentan-2-yl)-1H-indol-5-yl trifluoromethanesulfonate (17)

To a solution of 4-(methylthio)-1-(pentan-2-yl)-1H-indol-5-yltrifluoromethanesulfonate (13) (1.3 g, 3.4 mmol) in acetic acid (CH$_3$COOH, 5.0 mL) at around 5° C. was added hydrogen peroxide (H$_2$O$_2$, 30%, 0.42 ml, 3.7 mmol). The mixture was allowed to warm to room temperature, stirred overnight, and then concentrated to dryness in vacuo to give 4-(methylsulfinyl)-1-(pentan-2-yl)-1H-indol-5-yl trifluoromethanesulfonate (17) (1.32 g, 100%). $^1$H NMR (500 MHz, CD$_2$Cl$_2$): δ 7.58 (d, J=9.0, 1H), 7.45 (d, J=2.5 Hz, 1H), 7.35 (m, 1H), 7.13 (d, J=9.0, 1H), 4.57 (m, 1H), 3.07 (d, 3H), 1.87 (m, 2H), 1.55 (m, 3H), 1.26 (m, 2H), 0.92 (m, 3H). Mass (ESI, M+H): 398.4. See also Bronner, S. M.; Bahnck K. B.; Garg, N. K.; *Org. Lett.*, 11: 1007 (2009).

Synthesis of 5-(benzo[b]thiophen-2-yl)-4-(methylsulfinyl)-1-(pentan-2-yl)-1H-indole (19)

To a deaerated solution of 4-(methylsulfinyl)-1-(pentan-2-yl)-1H-indol-5-yltrifluoromethanesulfonate 17) (0.40 g, 1.0 mmol) and benzo[b]thiophen-2-ylboronic acid (18) (0.35 g, 2.0 mmol), and Pd(PPh$_3$)$_4$ (60 mg, 0.05 mmol) in toluene (10 mL) was added aqueous K$_2$CO$_3$ (2M, 6.0 mL). The mixture was heated at 90° C. for 4 h. Toluene (20 mL) was added and the organic phase was washed with water (20 mL) and then concentrated to dryness in vacuo. The residual was purified by silica gel column chromatography (2:1 hexanes/ethyl acetate) to give 5-(benzo[b]thiophen-2-yl)-4-(methylsulfinyl)-1-(pentan-2-yl)-1H-indole (19) (0.26 g, 68%) as a yellow oil. $^1$H NMR (500 MHz, CD$_2$Cl$_2$): δ 7.88 (d, J=8.0, 1H), 7.85 (d, J=8.0 Hz, 1H), 7.58 (d, J=8.5 Hz, 1H), 7.40 (m, 4H), 7.35 (d, J=3.5, 1H), 7.2 9s, 1H), 4.62 (m, 1H), 3.00 (d, 3H), 1.88 (m, 2H), 1.57 (m, 3H), 1.24 (m, 2H), 0.93 (m, 3H). Mass (ESI, M+H): 382.7. See also Im, G-Y. J., et al., *J. Am. Chem. Soc.*, 132:17933 (2010).

Synthesis of mono-InBTBT (20)

Trifluoromethanesulfonic acid (CF$_3$SO$_2$OH, 7.0 mL) was added to a mixture of 5-(benzo[b]thiophen-2-yl)-4-(methylsulfinyl)-1-(pentan-2-yl)-1H-indole (19) (0.250 g, 0.656 mmol) and phosphorus pentoxide (P$_2$O$_5$, 47 mg, 0.33 mmol) under nitrogen. The resulting mixture was stirred at room temperature for 48 hours. The mixture was then poured into crushed ice (50 g) and the resulting yellow solid was filtered and washed with water (20 mL) and methanol (5 mL). The yellow solid was baked at 80° C. in a vacuum oven for 3 h before purification by silica gel column chromatography (1:2 hexanes/chloroform) to give mono-InBTBT (20) (0.094 g, 41% yield) as a pale yellow solid.

Example 4

Synthetic Route to Furan Diels-Alder Adduct (25)

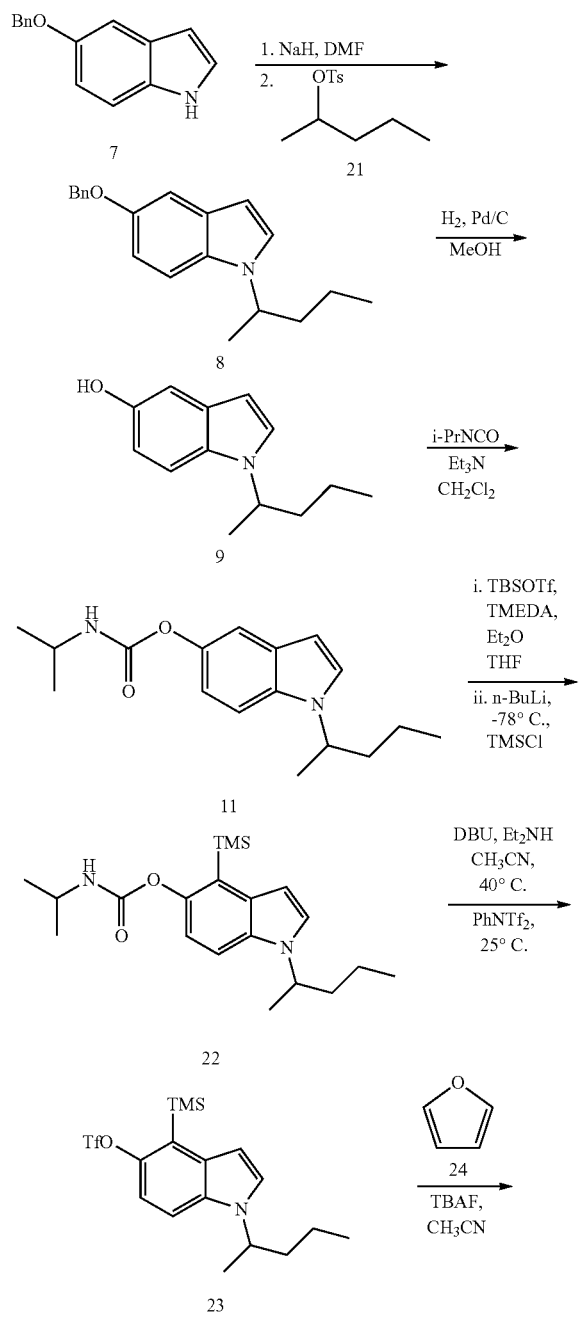

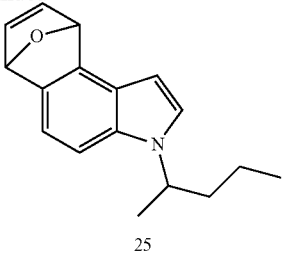

Synthesis of 5-(benzyloxy)-1-(pentan-2-yl)-1H-indole (8)

5-Benzyloxyindole (7) (8.81 g, 39.5 mmol, 1.0 equiv., supplied by Combi-Blocks) was dissolved in anhydrous DMF (100 mL) and the solution was cooled to 0° C. Dry sodium hydride (1.89 g, 78.9 mmol, 2.0 equiv.) was added slowly. The mixture was warmed to room temperature over 30 minutes. 2-Pentyl-tosylate was added dropwise. The mixture was stirred for 18 h. Water was added slowly (dropwise at first) to quench excess NaH. The resulting mixture was extracted once with ether, and then washed with water and brine, respectively. The organic phase was dried with MgSO$_4$, and concentrated on a rotary evaporator to yield a crude oil. The crude product was purified by flash column chromatography (3:1 hexanes/ethyl acetate) to yield 5-(benzyloxy)-1-(pentan-2-yl)-1H-indole (8) as an amber oil (10.67 g) of approximately 90% purity, which was used in the next step without any further purification. $^1$H NMR (500 MHz, CDCl$_3$) δ7.50 (d, J=7.3 Hz, 2H), 7.40 (t, J=7.3 Hz, 2H), 7.34 (d, J=7.3 Hz, 1H), 7.29 (d, J=9.0 Hz, 1H), 7.17 (dd, J=8.9, 2.4 Hz, 1H), 6.96 (dd, J=8.9, 2.4 Hz, 1H), 6.44 (d, J=3.1 Hz, 1H), 5.12 (s, 2H), 4.44 (m, 1H), 1.88 (m, 1H), 1.77 (m, 1H), 1.50 (d, J=6.8 Hz, 3H), 1.23 (m, 2H), 0.89 (t, J=7.4 Hz, 3H).

Synthesis of 1-(pentan-2-yl)-1H-indol-5-ol (9)

5-(Benzyloxy)-1-(pentan-2-yl)-1H-indole (8) (10.67 g, 36.4 mmol, 1.0 equiv.) was dissolved in MeOH (90 mL), and 10% wt. Pd/C was added (3.87 g, 3.64 mmol, 0.10 equiv). The reaction mixture was placed under a hydrogen atmosphere using double balloons, and stirred for 24 h at room temperature. The mixture was filtered through a Celite® pad and washed with (800 mL). The filtrate was concentrated to afford 1-(pentan-2-yl)-1H-indol-5-ol (9) as a brown oil, which was used without any further purification in the next step. $^1$H NMR (500 MHz, CDCl$_3$) δ7.23 (d, J=8.8 Hz, 1H), 7.15 (d, J=2.9 Hz, 1H), 7.03 (d, J=1.8 Hz, 1H), 6.77 (dd, J=8.7, 2.0 Hz, 1H), 6.39 (d, J=2.8 Hz, 1H), 4.52 (br, 1H), 4.42 (m, 1H), 1.87 (m, 1H), 1.76 (m, 1H), 1.49 (d, J=6.8 Hz, 3H), 1.23 (m, 2H), 0.88 (t, J=7.4 Hz, 3H).

Synthesis of 1-(pentan-2-yl)-1H-indol-5-yl isopropylcarbamate (11)

To a stirred solution of 1-(pentan-2-yl)-1H-indol-5-ol (9) in CH$_2$Cl$_2$ (180 mL) was added i-PrNCO (5.37 mL, 54.6 mmol, 1.5 equiv.) and NEt$_3$ (1.52 mL, 10.9 mmol, 0.30 equiv.), respectively. The reaction mixture was stirred at room temperature for 21 h, then concentrated to dryness in vacuo affording a dark, viscous liquid. The crude product was purified by flash column chromatography (2:1 hexanes/ethyl acetate) to give a beige solid, which was further purified by recrystallization from 100 mL of hexanes. Analytically pure product (11) was obtained as a white solid (6.29 g, 55% three-step yield). $^1$H NMR (500 MHz, CDCl$_3$) δ 7.33 (d, J=2.1 Hz, 1H), 7.31 (d, J=8.9 Hz, 1H), 7.19 (dd, J=8.8, 2.2 Hz, 1H), 6.47 (d, J=3.1 Hz, 1H), 4.83 (d, J=6.6 Hz, 1H), 4.45 (m, 1H), 3.91 (m, 1H), 1.87 (m, 1H), 1.76 (m, 1H), 1.48 (d, J=6.8 Hz, 3H), 1.30-1.13 (m, 8H), 0.87 (t, J=7.4 Hz, 3H).

Synthesis of 4-(trimethylsilyl)-1-(pentan-2-yl)-1H-indol-5-yl isopropylcarbamate (22)

To a stirred solution of 1-(pentan-2-yl)-1H-indol-5-yl isopropylcarbamate (11) (5.752 g, 19.9 mmol, 1.0 equiv.) in Et$_2$O (143 mL) and THF (48 mL) was added TMEDA (4.19 mL, 27.9 mmol, 1.4 equiv.), and the solution was cooled to 0° C. Then, a solution of TBSOTf (5.50 mL, 23.9 mmol, 1.2 equiv.) in n-pentane (16 mL) was added, and the reaction mixture was left to stir for 5 minutes at 0° C., at which point the ice bath was removed and the reaction was stirred for 45 additional minutes. TMEDA (8.97 mL, 59.8 mmol, 3.0 equiv.) was added and the mixture was cooled to −78° C., followed by the slow addition of n-BuLi (2.5 M in hexanes, 23.9 mL, 59.8 mmol, 3.0 equiv.) over 10 minutes. The reaction mixture was stirred at −78° C. for 3 h before chlorotrimethylsilane (TMSCl, 17.4 mL, 140 mmol, 7.0 equiv.) was added slowly over 15 minutes. The reaction mixture was stirred at −78° C. for an additional 1 h. The reaction mixture was quenched with 4 mL of MeOH, followed by 200 mL of 2 M hydrochloric acid, and allowed to warm to room temperature over 1 h with vigorous stirring. Diethylether (100 mL) was added, and the organic phase was separated. The organic phase was washed with 100 mL of water, 100 mL of brine, dried over MgSO$_4$ and concentrated. The crude material was purified via column chromatography (hexane:EtOAc, (gradient of 19:1→15:1→9:1, v/v)) to give 4-(trimethylsilyl)-1-(pentan-2-yl)-1H-indol-5-yl isopropylcarbamate (22) as a very viscous colorless liquid (6.15 g, 86%). $^1$H NMR (500 MHz, CDCl$_3$) δ 7.34 (d, J=8.8 Hz, 1H), 7.21 (d, J=3.3 Hz, 1H), 6.91 (d, J=8.8 Hz, 1H), 6.66 (d, J=3.2 Hz, 1H), 4.75 (d, J=8.0 Hz, 1H), 4.46 (m, 1H), 3.94 (m, 1H), 1.87 (m, 1H), 1.76 (m, 1H), 1.47 (d, J=6.8 Hz, 3H), 1.30-1.15 (m, 8H), 0.88 (t, J=7.4 Hz, 3H), 0.41 (s, 9H).

Synthesis of 4-(trimethylsilyl)-1-(pentan-2-yl)-1H-indol-5-yl trifluoromethanesulfonate (23)

To a stirred solution of 4-(trimethylsilyl)-1-(pentan-2-yl)-1H-indol-5-yl isopropylcarbamate (22) (1.40 g, 3.88 mmol, 1.0 equiv.) in MeCN (35 mL), DBU (1.45 mL, 9.71 mmol, 2.5 equiv.) and Et$_2$NH (0.60 mL, 5.82 mmol, 1.5 equiv.) were added, respectively. The solution was heated to 40° C. and stirred for 50 minutes before it was cooled to room temperature. Then, a solution of PhNTf$_2$ (2.08 g, 5.82 mmol, 1.5 equiv.) in MeCN (11 mL) was added, and the reaction mixture was stirred for an additional 80 minutes. The reaction mixture was passed through a silica gel plug and washed with EtOAc. The filtrate was concentrated and further purified by column chromatography (30:1 hexanes/EtOAc, v/v) to give 4-(trimethylsilyl)-1-(pentan-2-yl)-1H-indol-5-yltrifluoromethanesulfonate (23) as a slightly green liquid (1.30 g, 82%). $^1$H NMR (500 MHz, CDCl$_3$) δ 7.37 (d, J=9.0 Hz, 1H), 7.30 (d, J=3.4 Hz, 1H), 7.13 (d, J=9.1 Hz, 1H), 6.72 (d, J=3.3 Hz, 1H), 4.47 (m, 1H), 1.87 (m, 1H), 1.79 (m, 1H), 1.50 (d, J=6.8 Hz, 3H), 1.31-1.15 (m, 2H), 0.88 (t, J=7.4 Hz, 3H), 0.50 (s, 9H).

Synthesis of Furan Diels-Alder Adduct (25)

To a solution of 4-(trimethylsilyl)-1-(pentan-2-yl)-1H-indol-5-yltrifluoromethanesulfonate (23) (529 mg, 1.30 mmol, 1.0 equiv) and furan (24) (0.47 mL, 6.5 mmol, 5.0 equiv) in MeCN (12 mL) was added a solution of tetrabutyl ammonium fluoride (TBAF, 1 M in THF, 2.6 mL, 2.60 mmol, 2.0 equiv). The reaction mixture was stirred at room temperature for 15 minutes, and then filtered through a pad of silica gel and washed with EtOAc (200 mL). The filtrate was concentrated and further purified by column chromatography (5:1 hexanes/EtOAc, v/v) to give the furan Diels-Alder adduct (25) (250 mg, 76%). $^1$H NMR (500 MHz, CDCl$_3$) δ 7.19 (m, 2H), 7.14 (m, 2H), 6.96 (d, J=8.1 Hz, 1H), 6.44 (dd, J=5.9, 3.3 Hz, 1H), 6.00 (br, 1H), 5.83 (br, 1H), 4.43 (m, 1H), 1.85 (m, 1H), 1.75 (m, 1H), 1.45 (m, 3H), 1.20 (m, 2H), 0.88 (t, J=7.3 Hz, 3H).

Example 5

Proposed Synthetic Route to Pyrrole-Containing Semiconductors

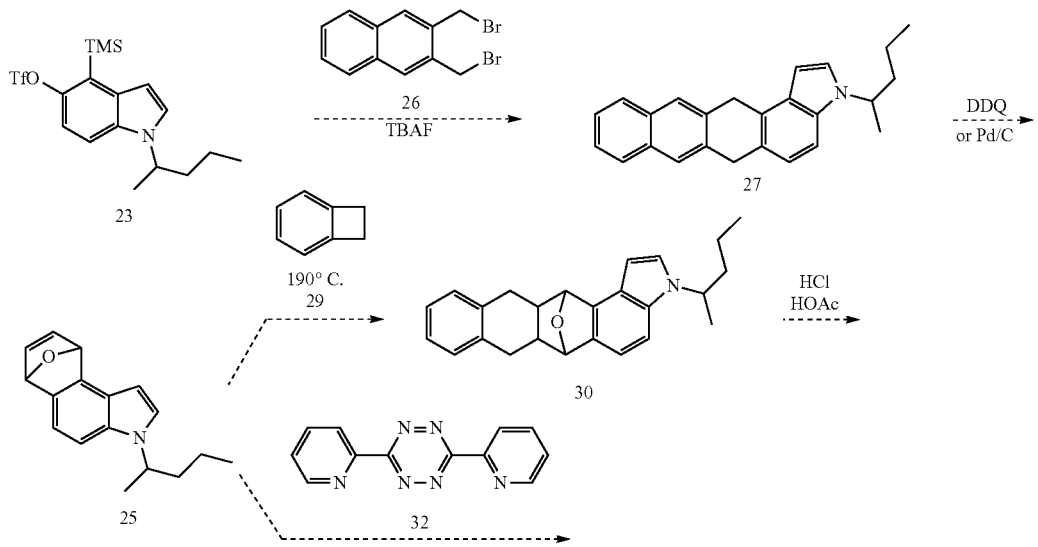

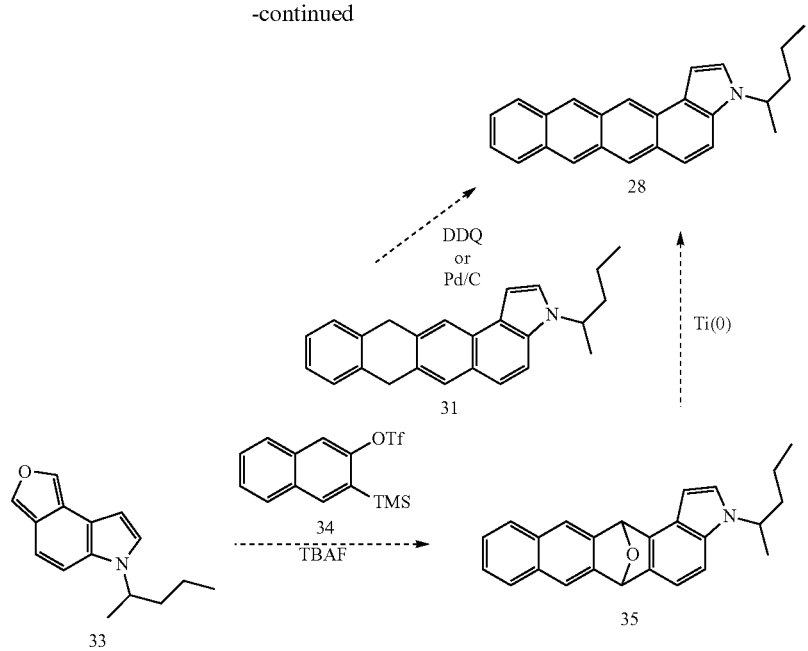
Compounds of formula (Ia) can be prepared according to the three proposed synthetic routes above starting from either 4-(trimethylsilyl)-1-(pentan-2-yl)-1H-indol-5-yl trifluoromethanesulfonate (23) or the furan Diels-Alder adduct (25).
Example 6
Proposed Alternative Synthetic Route to Pyrrole-Containing Semiconductors
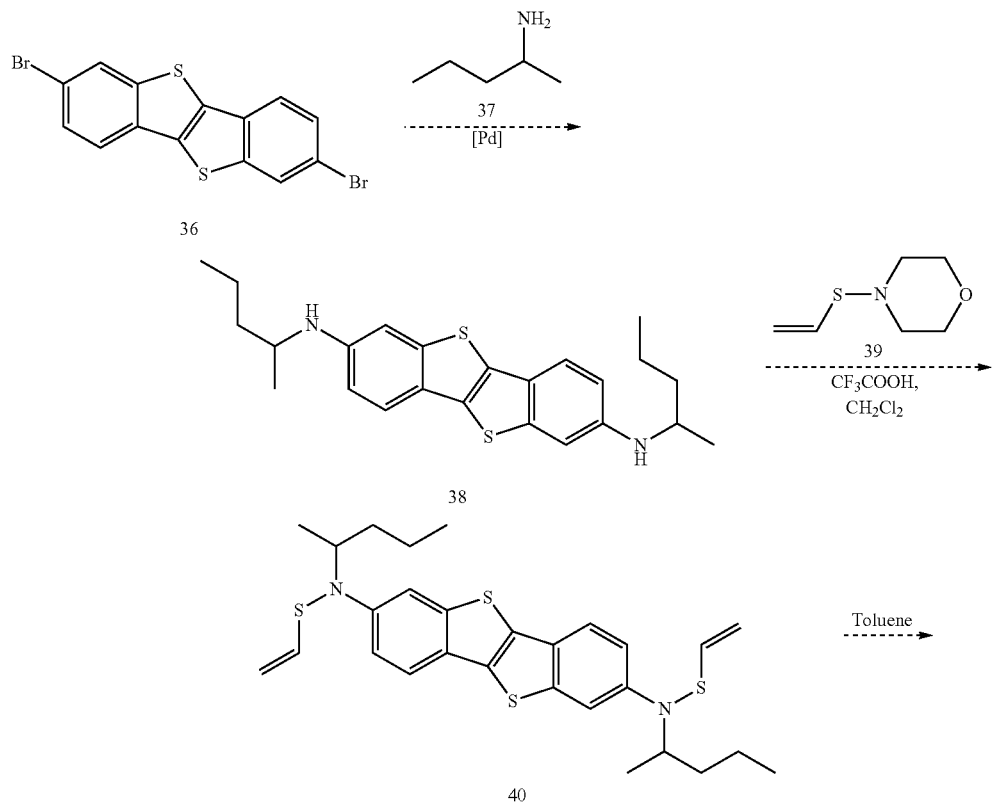

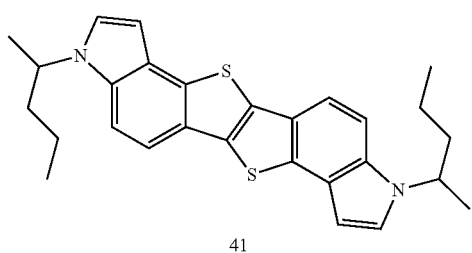

41

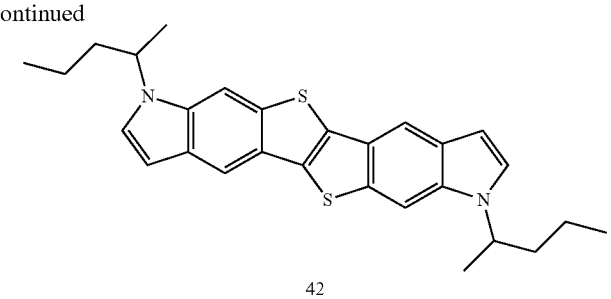

42

Compounds of formula (IIg) can be prepared according to the proposed synthetic route above starting from compound (36), which can be prepared according to procedures described in International Publication No. 2009113599, the disclosure of which is incorporated by reference herein. Compounds (40), (41), and (42) can be prepared according to the procedures described in Baudin et al., *Tetrahedron*, 43(5): 881-889 (1987), the disclosure of which is incorporated by reference herein.

Example 7

HOMO-LUMO Calculations

Table 1 below provides calculated HOMO and LUMO values of various compounds according to the present teachings.

TABLE 1

| R = Methyl | HOMO (eV) | LUMO (eV) |
|---|---|---|
| [pentacene structure] | −4.60 | −2.39 |
| [bis-indole fused structure] | −4.51 | −0.97 |
| [bis-indole fused structure] | −4.55 | −1.04 |
| [indole-anthracene structure] | −4.56 | −1.76 |
| [indole-thiophene fused structure] | −4.86 | −0.42 |

TABLE 1-continued

| R = Methyl | HOMO (eV) | LUMO (eV) |
|---|---|---|
| [indole-naphthacene structure] | −4.92 | −1.23 |
| [indole-thiophene-naphthalene structure] | −5.03 | −1.32 |
| [indole-chrysene structure] | −5.10 | −1.02 |
| [indole-picene structure] | −5.11 | −1.11 |

Example 8

Device Fabrication

Device Fabrication Procedure (Bottom Gate Top Contact (BGTC)): BGTC TFTs were fabricated using compounds of the present teachings as the semiconductor layer. N-doped silicon wafers (100) with 3000 Å thermally grown silicon dioxide layer (Addison Inc.) were used as device substrates. Prior to deposition of the semiconductor, the Si/SiO$_2$ surfaces were modified either through hexamethyldisilazane (HMDS) treatment or a poly(methyl methacrylate (PMMA) buffer layer. Thin films of semiconductors approximately 40-120 nm in thickness were prepared through physical vapor deposition (PVD), with the deposition rate of 0.1-0.5 Å/s and the substrate temperature of 30-120° C. The TFTs were completed by vapor deposition of 300 Å gold source/drain electrodes onto the semiconductor layer through a stencil mask to define the transistor channel. The channel lengths and widths are about 50-200 μm and about 500-2000 μm, respectively. The silicon dioxide layer served as the gate insulator. The gate electrode was accessed through an ohmic contact to the doped silicon.

All devices were characterized in a Signatone Probe Station using a Keithley 4200 Semiconductor Characterization System to obtain transfer and output characteristics. Device parameters were extracted from the transfer characteristics according to standard transistor equations.

Figure 2:
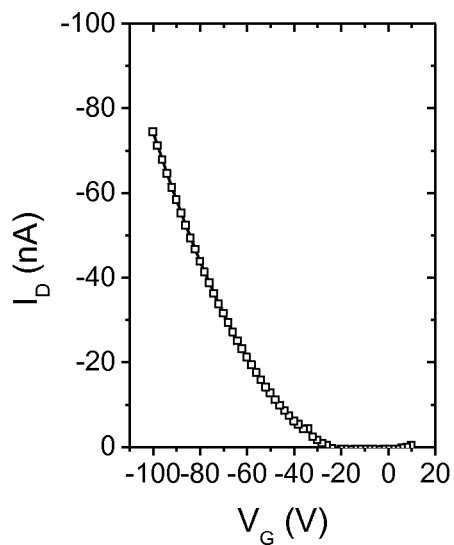
FIG. 2A shows representative Locus curves derived from a bottom gate top contact thin film transistor device incorporating a semiconductor film prepared from compound (6) according to the present teachings and an HMDS-treated $SiO_2$ gate insulator ($V_D=-100V$).
FIG. 2B shows representative Locus curves derived from a bottom gate top contact thin film transistor device incorporating a semiconductor film prepared from compound (6) according to the present teachings and a PMMA-modified $SiO_2$ gate insulator ($V_D=-100V$).
Figure 2:
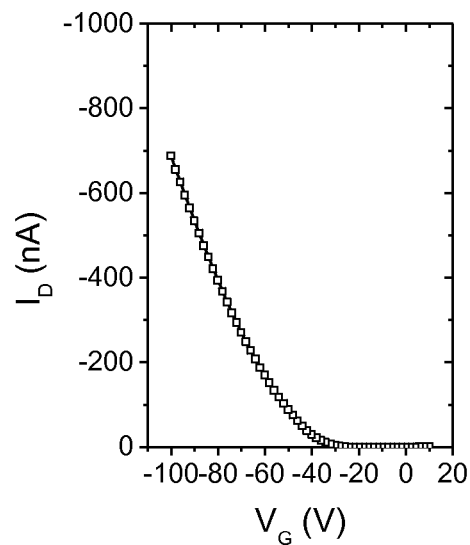

FIGS. 2A and 2B provide representative Locus curves derived from a bottom gate top contact thin film transistor device incorporating a semiconductor film prepared from compound (6) according to the present teachings and an HMDS-treated $SiO_2$ gate insulator (Device 1) and a PMMA-modified $SiO_2$ gate insulator (Device 2), respectively ($V_D$=−100V). Device 1 exhibits a hole mobility $\mu_p$~0.0003 $cm^2/Vs$ and a threshold voltage $V_{th}$~−40 V ($T_{sub}$=room temperature). Device 2 exhibits a hole mobility $\mu_p$~0.003 $cm^2/Vs$ and a threshold voltage $V_{th}$~−40 V ($T_{sub}$=room temperature).

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound selected from the group consisting of:

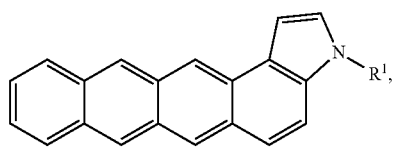
(Ia)

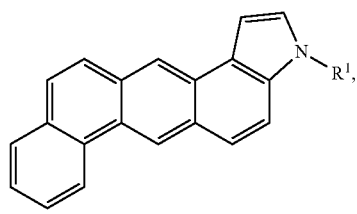
(Ib)

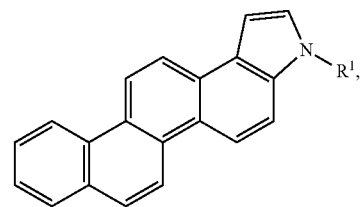
(Ic)

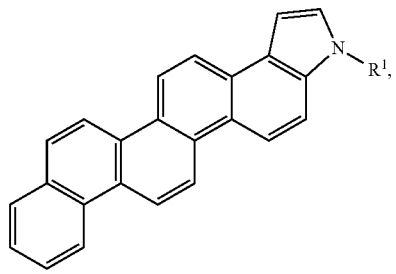
(Id)

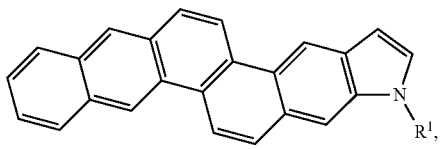
(Ie)

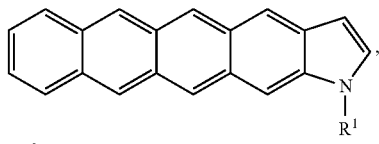
(If)

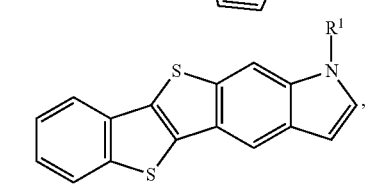
and wherein:
$R^1$ is a $C_{1-40}$ alkyl or haloalkyl group.

2. The compound of claim 1, wherein $R^1$ is a branched $C_{3-20}$ alkyl or haloalkyl group.

3. The compound of claim 1, wherein $R^1$ is a branched $C_{3-20}$ alkyl group.

4. The compound of claim 1, wherein $R^1$ is CHR'R", wherein R' is a linear $C_{3-12}$ alkyl or haloalkyl group; and R" is selected from $CH_3$, $CF_3$, $C_2H_5$, $CH_2CF_3$, $CF_2CH_3$, and $C_2F_5$.

5. A thin film semiconductor comprising a compound of claim 1.

6. A composite comprising a substrate and the thin film semiconductor of claim 5 deposited on the substrate.

7. An electronic device, an optical device, or an optoelectronic device comprising the thin film semiconductor of claim 5.

8. A field effect transistor device comprising a source electrode, a drain electrode, a gate electrode, and the thin film semiconductor of claim 5 in contact with a dielectric material.

9. The field effect transistor device of claim 8, wherein the field effect transistor has a structure selected from top-gate bottom-contact structure, bottom-gate top-contact structure, top-gate top-contact structure, and bottom-gate bottom-contact structure.

10. The field effect transistor device of claim 8, wherein the dielectric material comprises an organic dielectric material.

11. The field effect transistor device of claim 8, wherein the dielectric material comprises an inorganic dielectric material or a hybrid organic/inorganic dielectric material.

12. An electroluminescent display device comprising a plurality of field effect transistors according to claim 8.

13. An organic light-emitting transistor comprising a source electrode, a drain electrode, a gate electrode, and an active layer in contact with a dielectric material, wherein the active layer comprises a compound of claim 1.

14. The organic light-emitting transistor of claim 13, wherein the active layer further comprises a second semiconducting compound different from the compound of claim 1.

15. The organic light-emitting transistor of claim 13, wherein the active layer further comprises a light-emitting compound different from the compound of claim 1.

16. The device of claim 7, wherein the thin film semiconductor comprises the compound

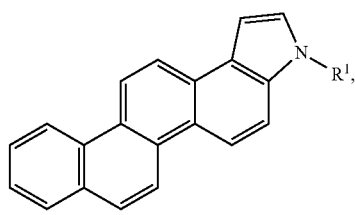

wherein $R^1$ is a branched $C_{3-20}$ alkyl group.

17. The device of claim 7, wherein the thin film semiconductor comprises the compound

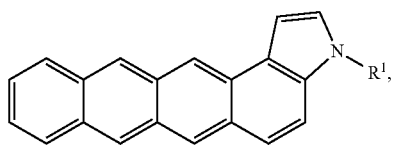

wherein $R^1$ is a branched $C_{3-20}$ alkyl group.

18. The device of claim 7, wherein the thin film semiconductor comprises the compound

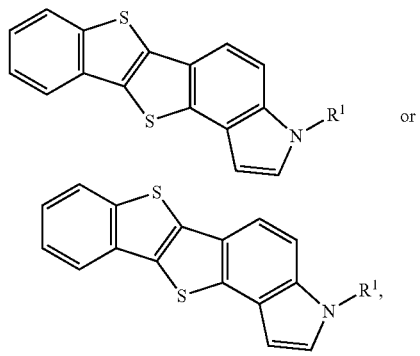

wherein $R^1$ is a branched $C_{3-20}$ alkyl group.

19. The device of claim 7, wherein the thin film semiconductor comprises the compound

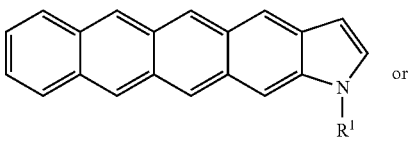

or

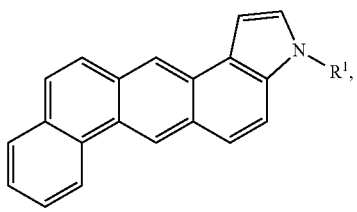

wherein $R^1$ and $R^2$ independently a branched $C_{3-20}$ alkyl group.

20. The device of claim 7, wherein the thin film semiconductor comprises the compound

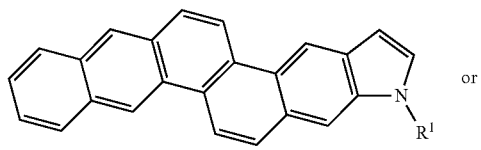

or

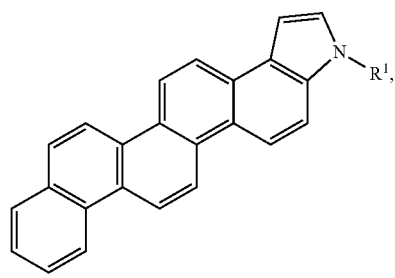

wherein $R^1$ and $R^2$ independently a branched $C_{3-20}$ alkyl group.

* * * * *